(12) United States Patent
Ferree

(10) Patent No.: US 6,706,068 B2
(45) Date of Patent: Mar. 16, 2004

(54) ARTIFICIAL DISC REPLACEMENTS WITH NATURAL KINEMATICS

(76) Inventor: Bret A. Ferree, 1238 Cliff Laine Dr., Cincinnati, OH (US) 45208

(*) Notice: Subject to any disclaimer, the term of this patent is extended or adjusted under 35 U.S.C. 154(b) by 0 days.

(21) Appl. No.: 10/420,423

(22) Filed: Apr. 22, 2003

(65) Prior Publication Data

US 2003/0199981 A1 Oct. 23, 2003

Related U.S. Application Data

(60) Provisional application No. 60/374,747, filed on Apr. 23, 2002, provisional application No. 60/445,958, filed on Feb. 7, 2003, and provisional application No. 60/449,642, filed on Feb. 24, 2003.

(51) Int. Cl.⁷ ............................................. A61F 2/44
(52) U.S. Cl. ....................................... 623/17.11
(58) Field of Search .............................. 623/17.11, 17.14, 623/17.15, 17.16, 20.14, 20.22, 20.24; 606/61

(56) References Cited

U.S. PATENT DOCUMENTS

| | | | |
|---|---|---|---|
| 4,759,766 A | 7/1988 | Buettner-Janz et al. | 623/17 |
| 5,258,031 A * | 11/1993 | Salib et al. | 623/17 |
| 5,314,477 A | 5/1994 | Marnay | 623/17 |
| 5,401,269 A * | 3/1995 | Buttner-Janz et al. | 623/17 |
| 5,425,773 A | 6/1995 | Boyd et al. | 623/17 |
| 5,507,816 A | 4/1996 | Bullivant | 623/17 |
| 5,534,029 A | 7/1996 | Shima | 623/17 |
| 5,556,431 A | 9/1996 | Buttner-Janz | 623/17 |
| 5,562,738 A * | 10/1996 | Boyd et al. | 623/17 |
| 5,676,701 A | 10/1997 | Yuan et al. | 623/17 |
| 5,755,796 A | 5/1998 | Ibo et al. | 623/17 |
| 5,895,428 A | 4/1999 | Berry | 623/17 |
| 6,019,792 A | 2/2000 | Cauthen | 623/17 |
| 6,039,763 A * | 3/2000 | Shelokov | 623/17 |
| 6,146,421 A * | 11/2000 | Gordon et al. | 623/17.15 |
| 6,235,060 B1 * | 5/2001 | Kubein-Meesenburg et al. | 623/20.13 |
| 6,325,828 B1 * | 12/2001 | Dennis et al. | 623/20.14 |
| 6,368,350 B1 | 4/2002 | Erickson et al. | 623/17.14 |
| 6,416,551 B1 | 7/2002 | Keller | 623/17.11 |
| 6,540,785 B1 * | 4/2003 | Gill et al. | 623/17.14 |

* cited by examiner

Primary Examiner—Eduardo C. Robert
Assistant Examiner—David Comstock
(74) Attorney, Agent, or Firm—Gifford, Krass, Groh, Sprinkle, Anderson & Citkowski, PC

(57) ABSTRACT

This invention improves upon prior art total disc replacements (TDRS) by more closely replicating the kinematics of a natural disc. The preferred embodiments feature two or more fixed centers of rotation (CORs) and an optional variable COR (VCOR) as the artificial disc replacements (ADRs) translates from a fixed posterior COR to a more anterior COR. The multiple CORs permit a TDR with a posterior COR that lies posterior to the COR of the TDR to facilitate normal disc motion. The use of two or more CORs allow more flexion and more extension than permitted by the facet joints and the annulus fibrosis. Artificial facet joint-like components may also be incorporated into the design to restrict excessive translation, rotation, and/or lateral bending.

25 Claims, 9 Drawing Sheets

(NEUTRAL POSITION)

(5-DEG EXT)

(8-DEG FLEX)

ANTERIOR

LATERAL

INTERIOR EXPOSED

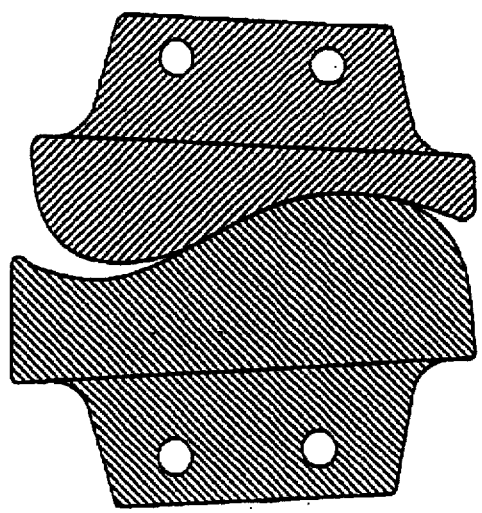
*Fig - 12A*
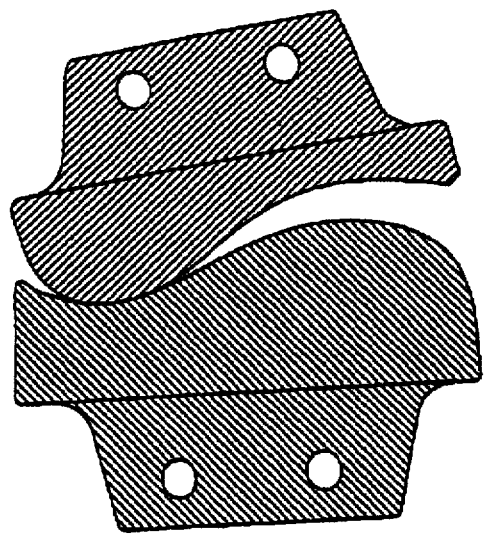
*Fig - 12B*
*Fig - 12C*
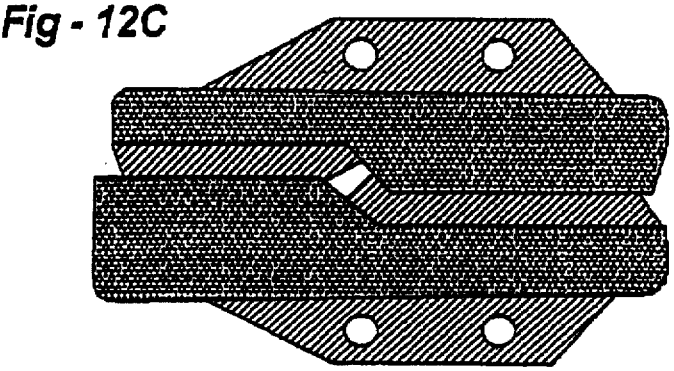

ARTIFICIAL DISC REPLACEMENTS WITH NATURAL KINEMATICS

REFERENCE TO RELATED APPLICATIONS

This application claims priority from U.S. Provisional Patent Application Serial Nos. 60/374,747, filed Apr. 23, 2002; 60/445,958, filed Feb. 7, 2003; and 60/449,642, filed Feb. 24, 2003. The entire content of each application is incorporated herein by reference.

FIELD OF THE INVENTION

This invention relates generally to artificial disc replacements (ADRs) and, more particularly, to ADRs facilitating more natural kinematics.

BACKGROUND OF THE INVENTION

Many spinal conditions, including degenerative disc disease, can be treated by spinal fusion or through artificial disc replacement (ADR). ADR has several advantages over spinal fusion. The most important advantage of ADR is the preservation of spinal motion. Spinal fusion eliminates motion across the fused segments of the spine. Consequently, the discs adjacent to the fused level are subjected to increased stress. The increased stress increases the changes of future surgery to treat the degeneration of the discs adjacent to the fusion. However, motion through an ADR also allows motion through the facet joints. Motion across arthritic facet joints could lead to pain following ADR. Some surgeons believe patients with degenerative disease and arthritis of the facet joints are not candidates for ADR.

Current ADR designs do not attempt to limit the pressure across the facet joints or facet joint motion. Indeed, prior art ADRs generally do not restrict motion. For example, some ADR designs place bags of hydrogel into the disc space which do not limit motion in any direction. In fact, ADRs of this kind may not, by themselves, provide sufficient distraction across the disc space. ADR designs with metal plates and polyethylene spacers may restrict translation but they do not limit the other motions mentioned above. The articular surface of the poly spacer is generally convex in all directions. Some ADR designs limit motion translation by attaching the ADR halves at a hinge.

One of the most important features of an artificial disc replacement (ADR) is its ability to replicate the kinematics of a natural disc. ADRs that replicate the kinematics of a normal disc are less likely to transfer additional forces above and below the replaced disc. In addition, ADRs with natural kinematics are less likely to stress the facet joints and the annulus fibrosus (AF) at the level of the disc replacement. Replicating the movements of the natural disc also decreases the risk of separation of the ADR from the vertebrae above and below the ADR.

The kinematics of ADRs are governed by the range of motion (ROM), the location of the center of rotation (COR) and the presence (or absence) of a variable center of rotation (VCOR). Generally ROM is limited by the facet joints and the AF. A natural disc has a VCOR, that is, the COR varies as the spine bends forward (flexion) and backward (extension). Typically, the vertebra above a natural disc translates forward 1–2 mm as the spine is flexed.

Prior art total disc replacements (TDR), that is, ADRs with rigid plates that attach to the vertebrae, do not replicate the kinematics of the natural disc. Generally, the COR lies too anterior. Most prior art TDRs also rely on a single, fixed COR. As a result, many of the prior art TDRs have a limited ROM.

SUMMARY OF THE INVENTION

This invention improves upon prior art TDRs by more closely replicating the kinematics of a natural disc. The preferred embodiments feature two or more fixed centers of rotation (CORs) and an optional variable COR (VCOR) as the ADR translates from a fixed posterior COR to a more anterior COR.

The multiple CORs permit a TDR with a posterior COR that lies posterior to the COR of the TDR to facilitate normal disc motion. The use of two or more CORs allow more flexion and more extension than permitted by the facet joints and the AF. Artificial facet joint-like components may also be incorporated into the design to restrict excessive translation, rotation, and/or lateral bending.

BRIEF DESCRIPTION OF THE DRAWINGS

FIG. 12A is a sagittal cross section of yet a further embodiment of an artificial disc replacement according to the invention;

FIG. 12B is a sagittal cross section of the embodiment of the ADR of FIG. 12A;

FIG. 12C is a view of the side of the ADR of FIG. 12A;

DETAILED DESCRIPTION OF THE INVENTION

My U.S. Provisional Patent Application Serial No. 60/374,747, incorporated herein by reference, describes various improved artificial disc replacements (ADRs), including various embodiments that restrict spinal extension, rotation, translation, and/or lateral bending. In one disclosed configuration, rotation and translocation are limited by a "spoon-on-spoon" type of cooperation. Wedge or trapezoid-shaped ADRs are also presented to preserve lordosis. Fasteners may be used to fix the ADR to upper and lower vertebrae. An optional lip may additionally be provided to prevent the trapping of soft tissue during the movement from a flexion to neutral position.

The present invention extends such teachings through total disc replacements (TDRs) that more closely replicate the kinematics of a natural disc. The preferred embodiments feature two or more fixed centers of rotation (CORs) and an optional variable COR (VCOR) as the ADR translates from a fixed posterior COR to a more anterior COR. The multiple CORs permit a TDR with a posterior COR that lies posterior to the COR of the TDR to facilitate normal disc motion. The use of two or more CORs allow more flexion and more extension than permitted by the facet joints and the AF. Artificial facet joint-like components may also be incorporated into the design to restrict excessive translation, rotation, and/or lateral bending.

Figure 1:
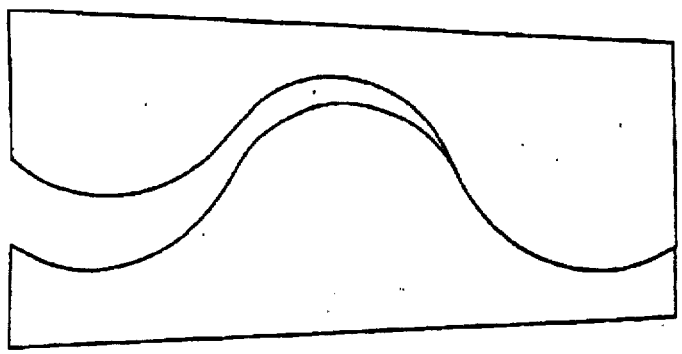
FIG. 1 is a sagittal cross section of a total disc replacement (TDR) according to the invention having three fixed centers of rotation (CORs)
Figure 2:
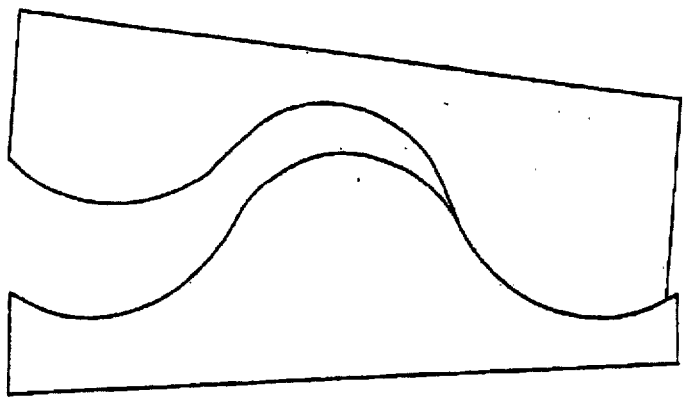
FIG. 2 is a sagittal cross section of the TDR of FIG. 1 extended 5 degrees, more or less.
Figure 3:
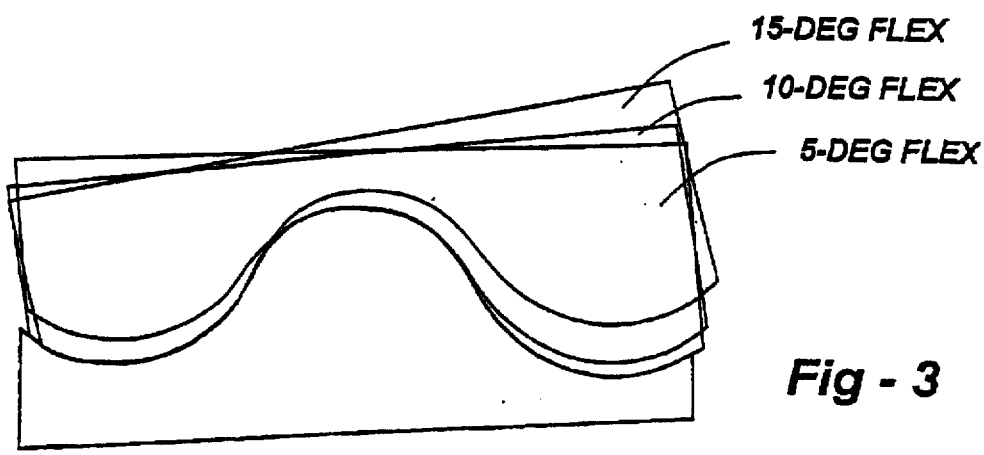
FIG. 3 is a sagittal cross section of the TDR of FIG. 1 showing various degrees of flexion.

FIG. 1 is a sagittal cross section of a TDR according to the invention having three fixed CORs. Articulation occurs at the posterior COR when the spine is in a neutral to extended position. FIG. 2 is a sagittal cross section of the TDR drawn in FIG. 1 with the ADR extended 5 degrees, more or less. FIG. 3 is a sagittal cross section of the TDR drawn in FIG. 1 in various degrees of flexion. As illustrated in the figure, the COR migrates anteriorly from a more posterior COR to a more anterior COR as the TDR is flexed.

Figure 4:
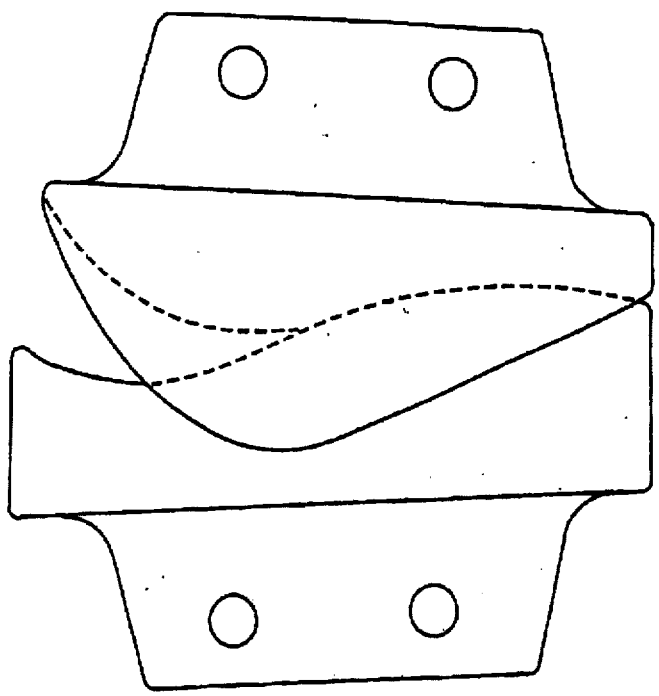
FIG. 4 is a sagittal cross section of another embodiment of a TDR having an anterior COR and a posterior COR.
Figure 5:
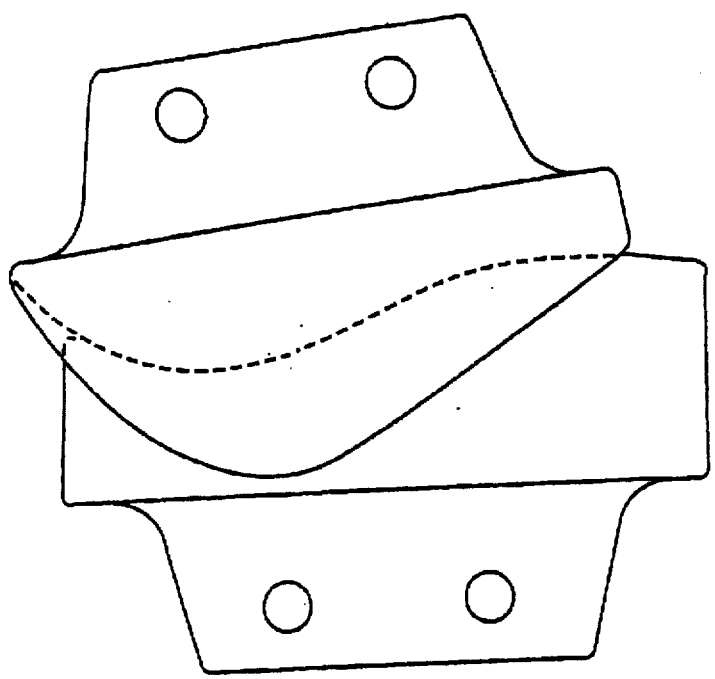
FIG. 5 is a sagittal cross section of the TDR of FIG. 4 in a flexed position.
Figure 6A:
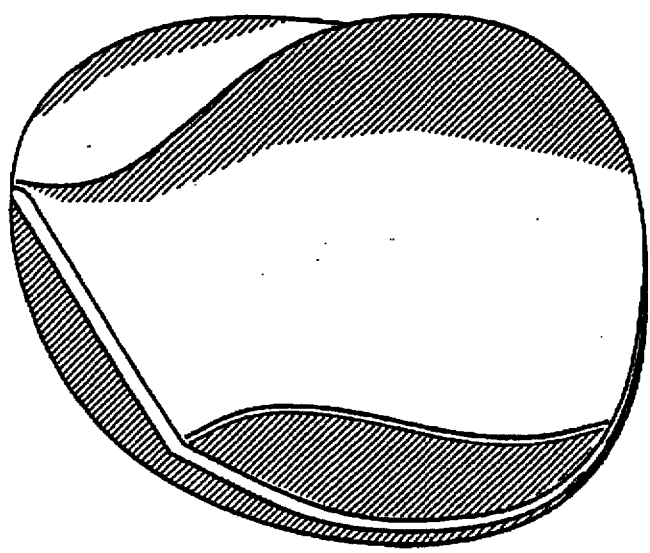
FIGS. 6A and 6B are drawings that show the articulating surfaces of the TDR drawn in FIG. 4.
Figure 6B:
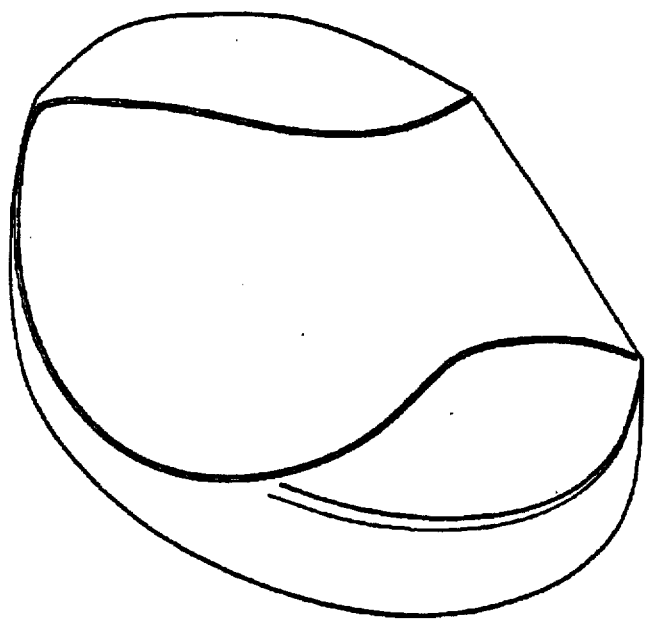

FIG. 4 is a sagittal cross section of another embodiment of the invention having an anterior COR and a posterior COR. In this case, the TDR articulates at the posterior COR with the TDR in neutral to extended position. FIG. 5 is a sagittal cross section of the TDR drawn in FIG. 4 in a flexed position. Note that the superior TDR endplate translates forward from the posterior COR to the anterior COR as the ADR moves from a neutral or extended position to a flexed position. FIGS. 6A and 6B are a view of the articulating surfaces of the TDR drawn in FIG. 4. The inferior TDR endplate is shown in FIG. 6A, and the inferior surface of the superior TDR endplate is shown in FIG. 6B.

Figure 7:
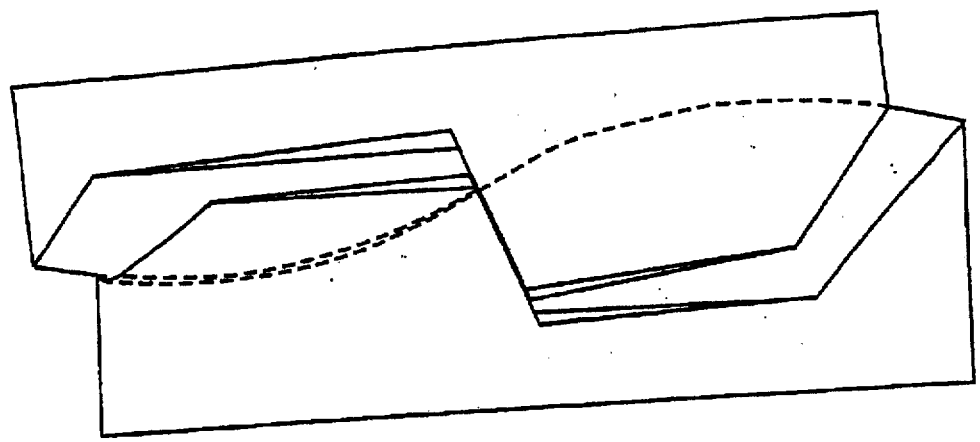
FIG. 7 is a sagittal cross section of another embodiment having an anterior and a posterior COR.
Figure 8:
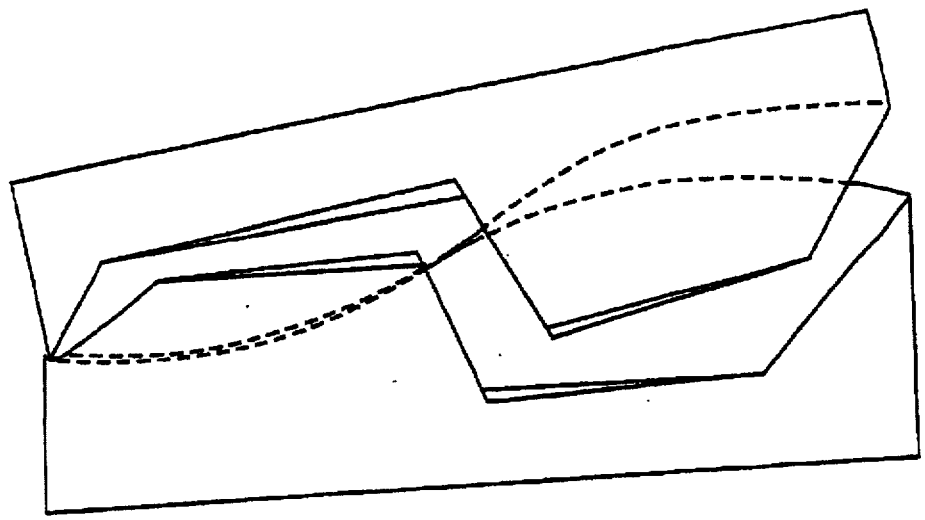
FIG. 8 is a sagittal cross section of the TDR of FIG. 7 in a more flexed position.
Figure 9:
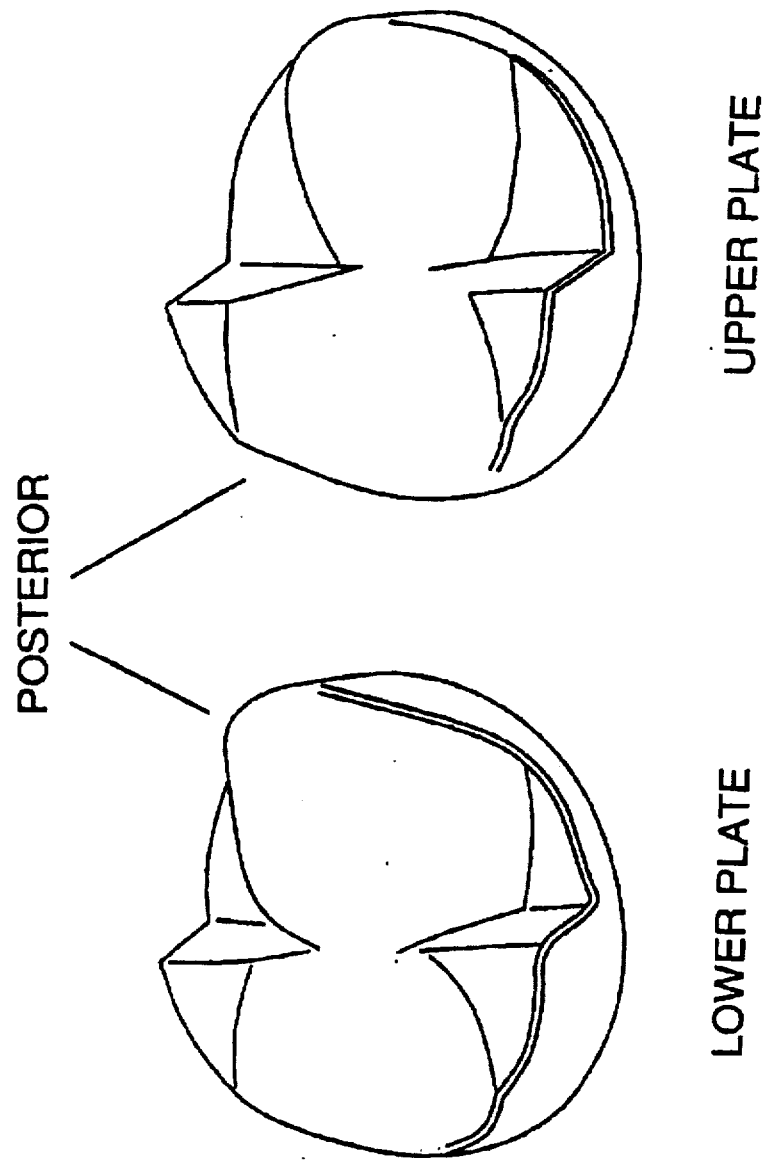
FIG. 9 is a view of the articulating surfaces of the TDR of FIG. 7.
Figure 10:
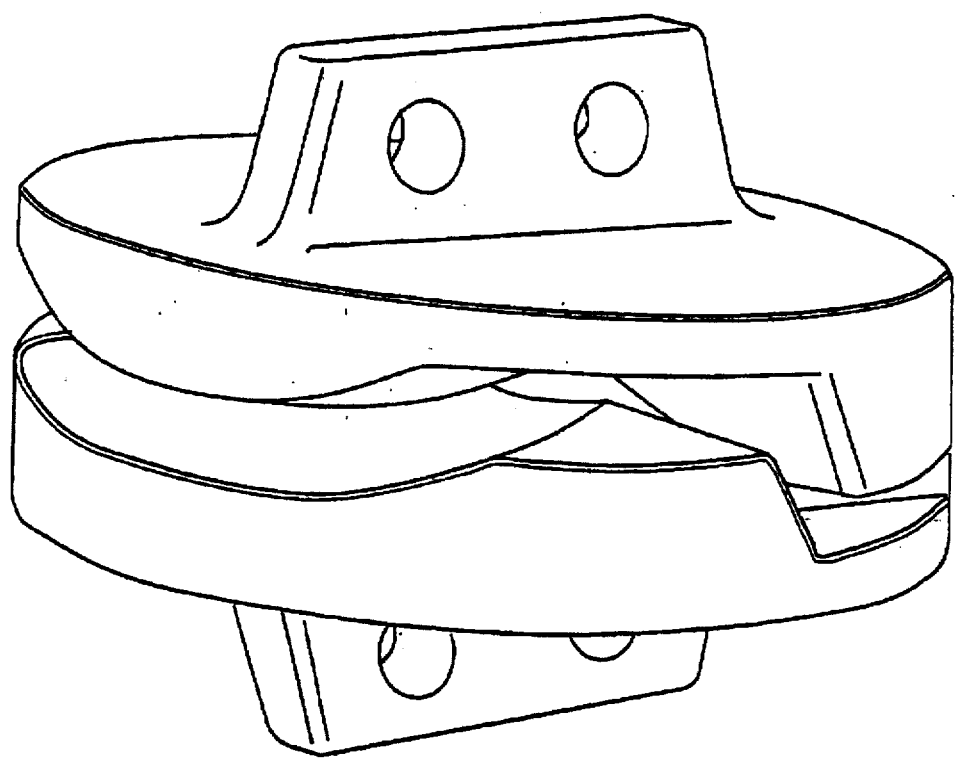
FIG. 10 is an oblique view of the assembled TDR drawn in FIG. 7.

FIG. 7 is a sagittal cross section of a further embodiment of the invention, including an anterior and a posterior COR. The design also includes novel artificial facet joint-like components that prevent excessive translation, rotation, or lateral bending. FIG. 8 is a sagittal cross section of the TDR drawn in FIG. 7 in a more flexed position. The drawing illustrates a gap between the artificial facet joint-like portions of the device. FIG. 9 is a view of the articulating surfaces of the TDR drawn in FIG. 7. The superior surface of the inferior TDR endplate is drawn on the left. FIG. 10 is an oblique view of the assembled TDR drawn in FIG. 7. This embodiment of the TDR illustrates the use of a toroidal patch and two spherical patches to form the anterior articulating surface of the lower plate. The novel torodial-spherical surface facilitates lateral bending.

Figure 11A:
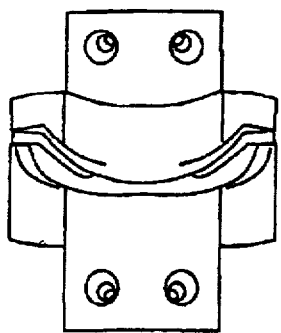
FIG. 11A is a view of the anterior side of a cervical embodiment of the TDR of FIG. 7.
Figure 11B:
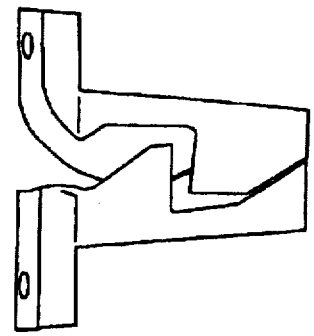
FIG. 11B is a view of the lateral side of the TDR of FIG. 11A.
Figure 11C:
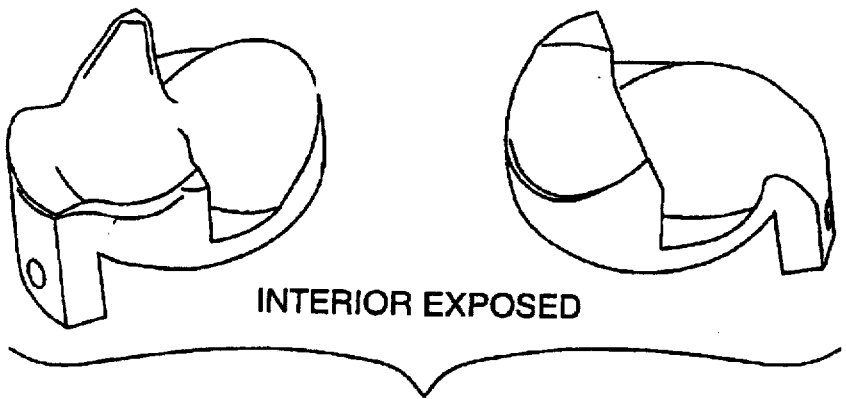
FIG. 11C is a view of the interior of the TDR drawn in FIG. 11A.

FIG. 11A is a view of the anterior side of a cervical embodiment of the TDR drawn in FIG. 7. Screws can be inserted through the holes in the TDR to attach the TDR to the vertebrae. A reversible locking mechanism can be used to prevent the screws from backing out of the vertebrae. FIG. 11B is a view of the lateral side of the TDR drawn in FIG. 11A. FIG. 11C is a view of the interior of the TDR drawn in FIG. 11A. The superior surface of the inferior component of the TDR is drawn on the left.

FIG. 12A is a sagittal cross section of another embodiment wherein, in contrast to the embodiment of FIG. 7, the articulating surfaces of the anterior and/or the posterior CORs are not congruent. The use of non-congruent articulating surfaces uncouples translation from rotation. ADRs with non-congruent joint surfaces allow greater spinal flexion and extension without corresponding subluxation of the vertebrae. The spherical projections from the upper and lower ADR endplates can cooperate to prevent the upper ADR endplate from translating posteriorly over the inferior ADR endplate. The drawing illustrates the different radius of curvature of the components forming the joint in the posterior aspect of the ADR.

FIG. 12B is a sagittal cross section of the embodiment of the ADR drawn in FIG. 12A in a flexed position. The drawing illustrates the different radius of curvature of the components forming the joint in the anterior aspect of the ADR. FIG. 12C is a view of the side of the ADR drawn in FIG. 12A. Artificial facet joint-like components, similar to those drawn in FIG. 7, prevent excessive forward translation of the upper ADR endplate relative to the lower ADR endplate. The artificial facet joint-like components can also limit axial rotation and lateral bending.

Figure 13A:
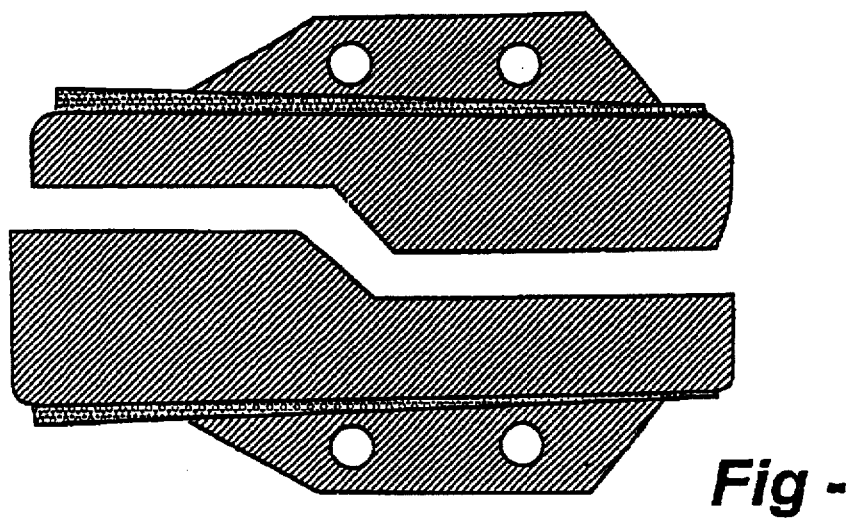
FIG. 13A is a view of the side of the ADR of FIG. 12A including modular shims.
Figure 13B:
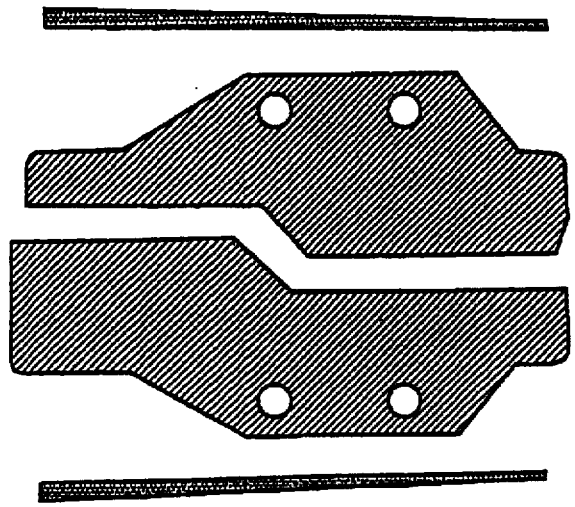
FIG. 13B is an exploded view of the embodiment of the ADR shown in FIG. 13A.

FIG. 13A is a view of the side of the ADR drawn in FIG. 12A, with modular sims. Modular shims can be used to increase the lordosis, or wedge shape, of the ADR. The modular shims can be attached to the top of the superior ADR endplate and/or the bottom of the inferior ADR endplate. The shims could fasten to the keels of the ADR. Alternatively, the shims could attach to another part of the ADR endplates. Lastly, the shims could simply lay on the ADR endplates. The shim inventory would include shims with different thickness and different angles. FIG. 13B is an exploded view of the embodiment of the ADR drawn in 13A.

Although surfaces depicted herein are shown as being 'congruent,' this is not necessary according to the invention. For example, a concave surface may have a radius of curvature that is larger than the radius of curvature of an articulating convex surface such that the two surfaces are not in direct or intimate contact at all times. Both symmetrical and asymmetrical joints may also be used. A portion of the back of the posterior joint may be removed to move the posterior COR further posterior and to increase the surface area of the posterior joint by increasing the radius of the surface. The articulating surface may be formed by a toroidal region and a spherical region, in this and other embodiments non-spherical surfaces may also be used to permit translation, rotation or other movements between more controlled articulations. TDRs according to the invention may be used in the cervical, thoracic, or lumbar spine.

ADR/TDRs according to this invention may also be composed of various materials. For example, the components may be constructed of a metal such as chrome cobalt or a ceramic such as aluminum oxide. The novel TDR can also be made of a metal or ceramic coated with a harder or softer second material. That is, one or both of the components may be a metal coated with a ceramic, or a metal or ceramic coated with a diamond-like material or other hardened surface. Alternatively, one or both of the components may be coated with a polymeric (i.e., polyethylene) surface or liner.

I claim:

1. An artificial disc replacement (ADR) configured for placement between the natural endplates of upper and lower vertebral bodies having anterior and posterior portions, the ADR comprising:

a superior component adapted for fixation to the upper vertebral body and providing lower articulating surface; and an inferior component adapted for fixation to the lower vertebral body and providing an upper articulating surface that cooperates with the lower surface;

one or more centers of rotation (CORs) located above the natural endplate of the upper vertebral body; and one or more centers of rotation (CORs) located below the natural endplate of the upper vertebral body.

2. The ADR of claim 1, wherein the lower articulating surface is convex and the upper articulating surface is concave.

3. The ADR of claim 1, wherein the lower and upper articulating surfaces are non-congruent.

4. The ADR of claim 1, further including at least one COR in the anterior portion and at least one COR in the posterior portion.

5. The ADR of claim 4, wherein the cooperation between the superior and inferior components relative to the anterior and posterior centers of rotation is spherical, symmetrical, or both.

6. The ADR of claim 4, wherein the anterior and posterior centers of rotation are at different vertical heights.

7. The ADR of claim 1, including a substantially smooth transition surface with respect to two or more of the CORs.

8. The ADR of claim 1, further including one or more physical features that limit translation, rotation and/or lateral bending.

9. The ADR of claim 1, wherein the two components do not have the same number of spherical surfaces.

10. An artificial disc replacement (ADR) having two or more centers of rotation (CORs) configured for placement between the natural endplates of upper and lower vertebral bodies, each having an anterior portion and a posterior portion, the ADR comprising:

a superior component adapted for fixation to the upper vertebral body and providing a lower articulating surface;

an inferior component adapted for fixation to the lower vertebral body and providing an upper articulating surface;

one or more centers of rotation (CORs) located above the natural endplate of the upper vertebral body; and one or more centers of rotation (CORs) located below the natural endplate of the upper vertebral body; and wherein one of the CORs is located between the posterior third and anterior two-thirds of the vertebral bodies.

11. The ADR of claim 10, wherein the lower articulating surface is convex and the upper articulating surface is concave.

12. The ADR of claim 10, wherein the lower and upper articulating surfaces are non-congruent.

13. The ADR of claim 10, further including at least one COR in the anterior portion and at least one COR in the posterior portion.

14. The ADR of claim 13, wherein the cooperation between the superior and inferior components relative to the anterior and posterior centers of rotation is spherical, symmetrical, or both.

15. The ADR of claim 10, including a substantially smooth transition surface with respect to two or more of the CORs.

16. The ADR of claim 10, further including one or more physical features that limit translation, rotation and/or lateral bending.

17. The ADR of claim 10, wherein the two components do not have the same number of spherical surfaces.

18. An artificial disc replacement (ADR) configured for positioning between vertebral bodies, comprising:

a superior component with a lower articulating surface; and an inferior component with an upper articulating surface that cooperates with the lower surface through an anterior-to-posterior-oriented toroidal region.

19. The ADR of claim 18, further including at least one spherical articulating region adjacent the toroidal region.

20. The ADR of claim 18, including a substantially smooth transition between the toroidal region and the spherical region.

21. The ADR of claim 18, wherein the lower and upper articulating surfaces are non-congruent.

22. The ADR of claim 18, further including at least one COR in the anterior portion and at least one COR in the posterior portion.

23. The ADR of claim 22, wherein the cooperation between the superior and inferior components relative to the anterior and posterior centers of rotation is spherical, symmetrical, or both.

24. The ADR of claim 18, further including one or more physical features that limit translation, rotation and/or lateral bending.

25. The ADR of claim 18, wherein the two components do not have the same number of spherical surfaces.

* * * * *

---

UNITED STATES PATENT AND TRADEMARK OFFICE
Certificate

Patent No. 6,706,068 B2           Patented: March 16, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Bret A. Ferree, Cincinnati, OH; and David Tompkins, Milford, OH.

KEVIN P. SHAVER
*Supervisory Patent Examiner*
Art Unit 3732